US00PP27453P2

(12) United States Plant Patent
Oostveen

(10) Patent No.: US PP27,453 P2
(45) Date of Patent: Dec. 13, 2016

(54) ***HIBISCUS* PLANT NAMED 'EXTREWHITEYE'**

(50) Latin Name: *Hibiscus moscheutos*
Varietal Denomination: Extrewhiteye

(71) Applicant: Cornelis A. Oostveen, De Kwakel (NL)

(72) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 0 days.

(21) Appl. No.: 14/545,813

(22) Filed: Jun. 23, 2015

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hibiscus* plant named 'Extrewhiteye', characterized by its relatively compact, upright and somewhat outwardly spreading plant form; moderately vigorous growth habit; palmately-lobed leaves; large white-colored flowers with red purple-colored centers; and good flower longeity.

2 Drawing Sheets

Botanical designation: *Hibiscus moscheutos*.
Cultivar denomination: 'EXTREWHITEYE'.

BACKGROUND OF THE INVENTION

The present invention relates to a new and distinct cultivar of *Hibiscus* plant, botanically known as *Hibiscus moscheutos*, commonly referred to as crimson-eyed rosemallow and hereinafter referred to by the name 'Extrewhiteye'.

The new *Hibiscus* plant is a product of a planned breeding program conducted by the Inventor in De Kwakel, The Netherlands. The objective of the breeding program is to create new compact *Hibiscus* plants with resistance to insect pests.

The new *Hibiscus* plant originated from a cross-pollination in August, 2012 in De Kwakel, The Netherlands of a proprietary selection of *Hibiscus moscheutos* identified as code number CB1133, not patented, as the female, or seed, parent with a proprietary selection of *Hibiscus moscheutos* identified as code number CB1214, not patented, as the male, or pollen, parent. The new *Hibiscus* plant was discovered and selected by the Inventor as a single flowering plant from within the progeny of the stated cross-pollination in a controlled greenhouse environment in De Kwakel, The Netherlands in August, 2013.

Asexual reproduction of the new *Hibiscus* plant by vegetative tip cuttings in a controlled greenhouse environment in De Kwakel, The Netherlands since September, 2013 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Extrewhiteye'. These characteristics in combination distinguish 'Extrewhiteye' as a new and distinct *Hibiscus* plant:

1. Relatively compact, upright and somewhat outwardly spreading plant form.
2. Moderately vigorous growth habit.
3. Dark green-colored leaves.
4. Large white-colored flowers with red purple-colored centers.
5. Good flower longevity.

Plants of the new *Hibiscus* can be compared to plants of the female parent selection. Plants of the new *Hibiscus* differ primarily from plants of the female parent selection in the following characteristics:

1. Plants of the new *Hibiscus* are more compact than and not as vigorous as plants of the female parent selection.
2. Plants of the new *Hibiscus* and the female parent selection differ in flower color as plants of the female parent selection have white-colored flowers with red-colored venation.

Plants of the new *Hibiscus* can be compared to plants of the male parent selection. Plants of the new *Hibiscus* differ primarily from plants of the male parent selection in the following characteristics:

1. Plants of the new *Hibiscus* are more freely branching than plants of the male parent selection.
2. Plants of the new *Hibiscus* have larger flowers than plants of the male parent selection.

Plants of the new *Hibiscus* can be compared to plants of *Hibiscus moscheutos* 'Sparkle', disclosed in U.S. Plant Pat. No. 21,798. In side-by-side comparisons conducted in De Kwakel, The Netherlands, plants of the new *Hibiscus* differed primarily from plants of 'Sparkle' in the following characteristics:

1. Plants of the new *Hibiscus* had thicker lateral branches than plants of 'Sparkle'.

2. Leaves of plants of the new *Hibiscus* were darker green in color than leaves of plants of 'Sparkle'.
3. Plants of the new *Hibiscus* and 'Sparkle' differed in flower color as plants of 'Sparkle' had white-colored flowers with red purple-colored centers and venation.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Extrewhiteye' grown in a container.

The photograph on the second sheet is a close-up view of a typical flower of 'Extrewhiteye'.

DETAILED BOTANICAL DESCRIPTION

The aforementioned photographs and following observations, measurements and values describe plants grown during the late summer in 23-cm containers in a glass-covered greenhouse in De Kwakel, The Netherlands and under cultural practices typical of commercial *Hibiscus* production. During the production of the plants, day temperatures ranged from 18° C. to 33° C. and night temperatures ranged from 18° C. to 25° C. Plants were 16 weeks old when the photographs and the description were taken. In the following description, color references are made to The Royal Horticultural Society Colour Chart, 2007 Edition, except where general terms of ordinary dictionary significance are used.

Botanical classification: *Hibiscus moscheutos* 'Extrewhiteye'.

Parentage:

*Female, or seed, parent*.—Proprietary selection of *Hibiscus moscheutos* identified as code number CB1133, not patented.

*Male or pollen parent*.—Proprietary selection of *Hibiscus moscheutos* identified as code number CB1214, not patented.

Propagation:

*Type*.—By vegetative tip cuttings.

*Time to initiate roots, summer*.—About seven days at temperatures about 22° C.

*Time to initiate roots, winter*.—About ten days at temperatures about 19° C.

*Time to produce a rooted young plant, summer*.—About three weeks at temperatures about 21° C.

*Time to produce a rooted young plant, winter*.—About four weeks at temperatures about 18° C.

*Root description*.—Medium in thickness, fibrous; white to light brown in color.

*Rooting habit*.—Freely branching; dense.

Plant description:

*Plant form and growth habit*.—Relatively compact, upright and somewhat outwardly spreading plant form, broad inverted triangular plant form; moderately vigorous growth habit.

*Branching habit*.—Moderate branching habit, usually about ten lateral branches develop; pinching enhances lateral branch development.

*Plant height*.—About 47 cm.

*Plant diameter* (*area of spread*).—About 71.5 cm.

Lateral branch description:

*Length*.—About 34.5 cm.

*Diameter*.—About 5 mm.

*Internode length*.—About 2.8 cm.

*Strength*.—Moderately strong.

*Aspect*.—Erect to about 40° from vertical.

*Texture*.—Moderately pubescent.

*Color*.—Close to 144A.

Leaf description:

*Arrangement*.—Alternate, single.

*Length*.—About 11.3 cm.

*Width*.—About 7.6 cm.

*Shape*.—Ovate.

*Apex*.—Apiculate.

*Base*.—Cordate.

*Margin*.—Irregularly crenate.

*Texture and luster, upper surface*.—Densely pubescent; matte.

*Texture and luster, lower surface*.—Smooth, glabrous; matte.

*Venation pattern*.—Pinnate.

*Color*.—Developing leaves, upper surface: Close to N137B. Developing leaves, lower surface: Close to 138B. Fully expanded leaves, upper surface: Darker than between 147A and 189A; venation, close to 144A. Fully expanded leaves, lower surface: Close to 147B; venation, close to 145B.

*Petioles*.—Length: About 7.6 cm. Diameter: About 3 mm. Texture, upper and lower surfaces: Smooth, glabrous. Color, upper and lower surfaces: Close to 144A.

Flower description:

*Flower arrangement*.—Large rotate flowers arranged singly at terminal leaf axils; freely flowering habit with about 50 flowers developing per plant during the flowering season; flowers face mostly outwardly to slightly upright.

*Fragrance*.—None detected.

*Flower longevity*.—Good flower longevity, flowers last for about four days; flowers not persistent.

*Natural flowering season*.—Plants flower from late summer into the autumn in The Netherlands; plants begin flowering about ten weeks after planting.

*Flower diameter*.—About 16.8 cm.

*Flower length* (*height*).—About 7 cm.

*Flower buds*.—Length: About 3.1 cm. Diameter: About 2.8 cm. Shape: Broadly ovate to almost deltoid. Color: Close to 143C; towards the apex, close to 150D.

*Petals*.—Arrangement: Corolla consists of five petals in a single whorl; petals imbricate. Length: About 9.5 cm. Width: About 9.5 cm. Shape: Broadly obovate. Apex: Rounded. Base: Attenuate. Margin: Entire. Texture, upper and lower surfaces: Smooth, glabrous. Luster, upper and lower surfaces: Slightly glossy; towards the base, moderately glossy. Color: When opening, upper surface: Close to NN155C; towards the base, close to between 53C and 60B; venation, close to NN155C. When opening, lower surface: Close to NN155C; venation, close to NN155C. Fully opened, upper surface: Close to between NN155B and N155C and becoming closer to NN155B with development; towards the base, close to 60A to 60B and becoming closer to 60A with development; venation, close to NN155B. Fully opened, lower surface: Close to between NN155B and N155C; venation, close to NN155B.

*Sepals*.—Appearance: Five sepals fused into a tubular star-shaped calyx. Length: About 3.3 cm. Width: About 2.4 cm. Shape: Broadly ovate. Apex: Broadly acute. Margin: Entire. Texture and luster, upper and lower surfaces: Smooth, glabrous; matte. Color: When opening and fully opened, upper surface: Close to between 143C and 145A. When opening and fully opened, lower surface: Close to 143C.

*Bracts*.—Quantity per flower: Ten in a single whorl. Length: About 1.8 cm. Width: About 3 mm. Shape: Lanceolate. Apex: Acute. Texture, upper and lower surfaces: Smooth, glabrous. Color, upper surface: Close to 143C. Color, lower surface: Close to 137C.

*Peduncles*.—Length: About 2.6 cm. Diameter: About 2.5 mm. Strength: Moderately strong. Angle: About 35° from the lateral branch axis. Texture: Smooth, glabrous. Color, upper and lower surfaces: Close to 143B.

*Reproductive organs*.—Androecium: Stamen number: Numerous, about 120. Filament length: About 3 mm. Filament color: Close to 155A and N155D. Anther shape: Orbicular. Anther length: About 1.5 mm. Anther color: Close to 155A. Amount of pollen: Abundant. Pollen color: Close to 1D. Gynoecium: Pistil length: About 3.5 cm. Style length: About 3.3 cm. Style color: Close to 155A. Stigma appearance: Five-parted, club-shaped. Stigma color: Close to 150D. Ovary color: Close to 145B.

*Seeds and fruits*.—Seed and fruit development have not been observed on plants of the new *Hibiscus*.

Temperature tolerance: Plants of the new *Hibiscus* have been observed to tolerate high temperatures of about 35° C. and to be hardy to USDA Hardiness Zone 6.

Pathogen & pest resistance: Plants of the new *Hibiscus* have not been observed to be resistant to pathogens and pests common to *Hibiscus* plants.

It is claimed:

1. A new and distinct *Hibiscus* plant named 'Extrewhit-eye' as illustrated and described.

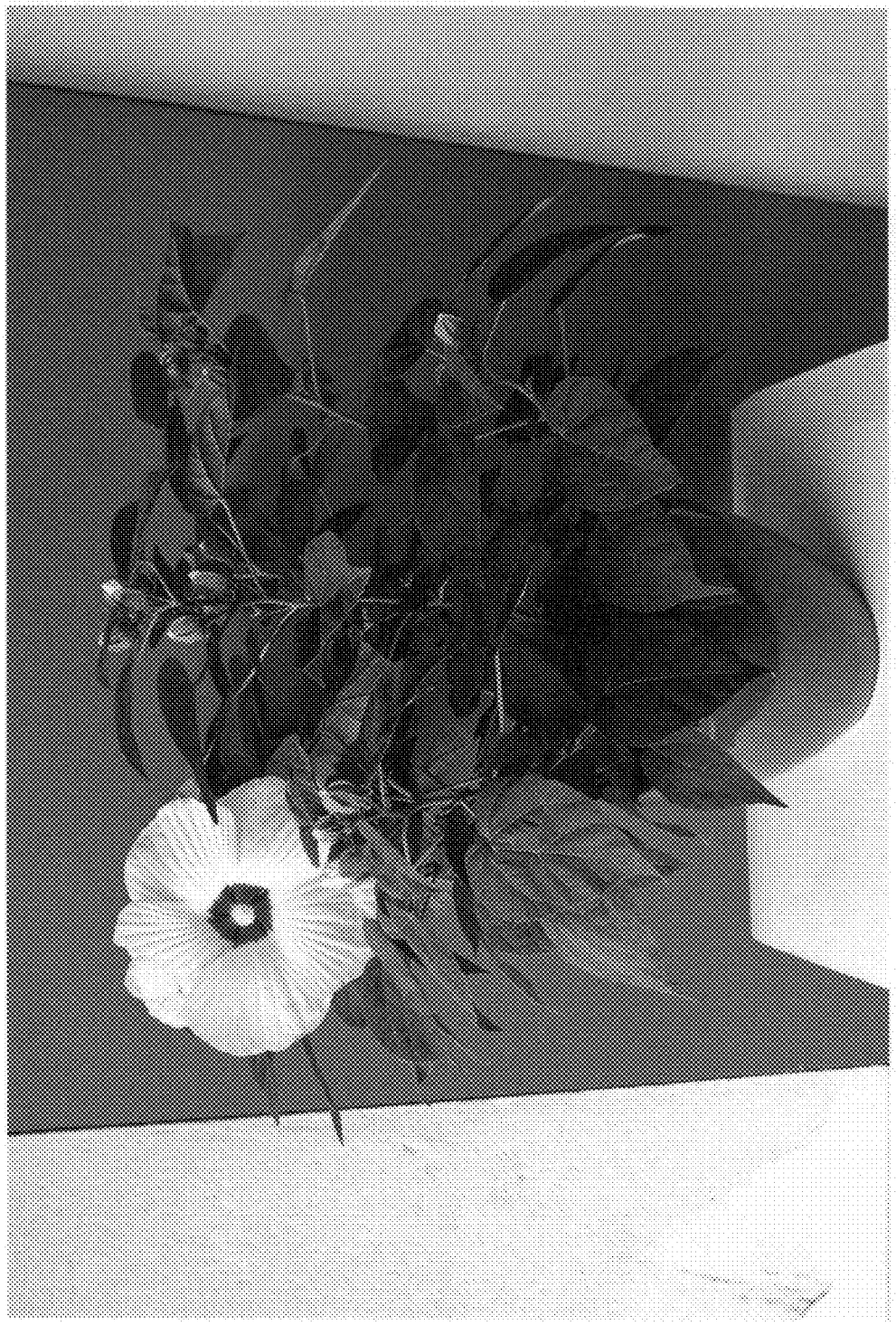

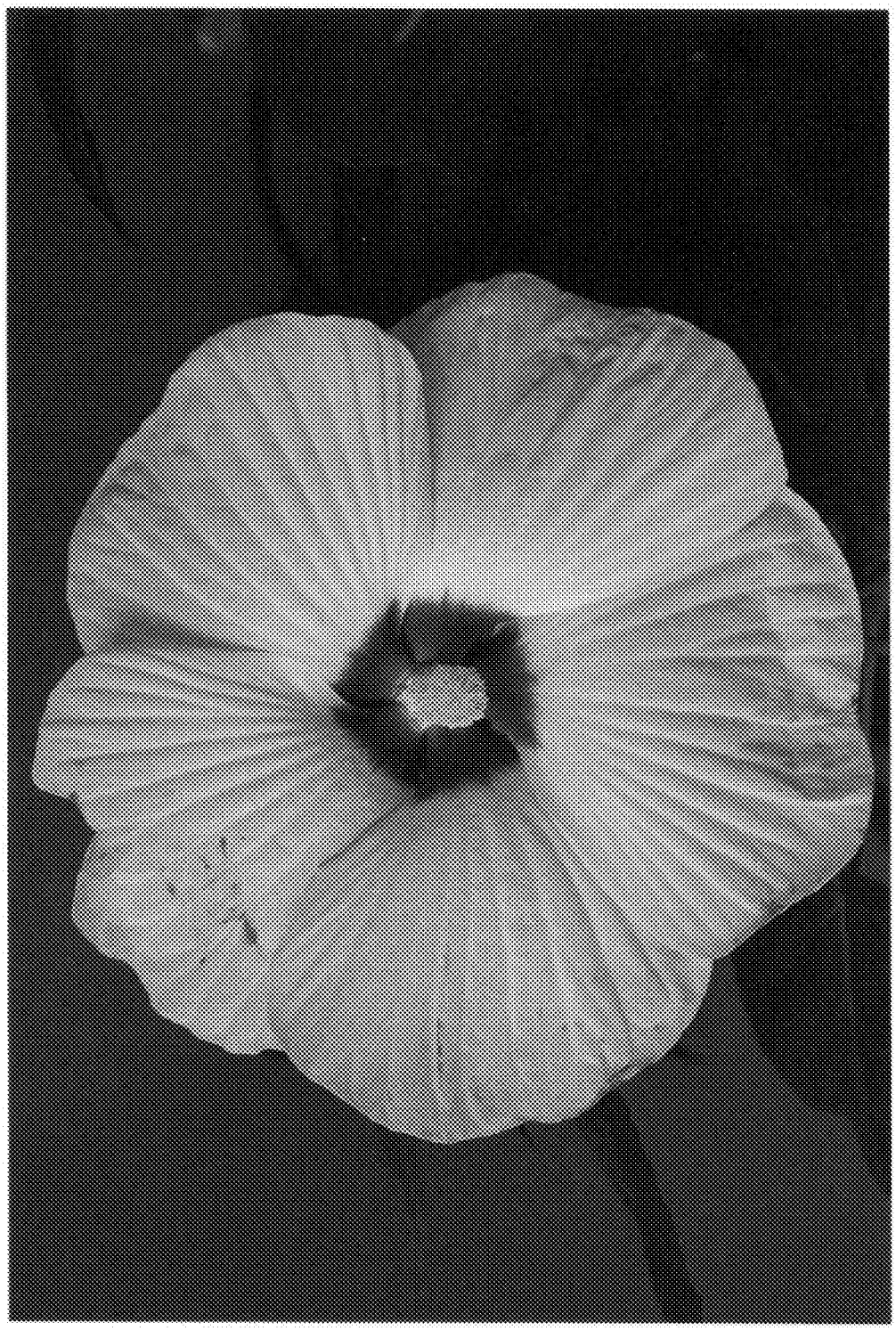

* * * * *